US012773553B2

(12) United States Patent
Mazanec

(10) Patent No.: US 12,773,553 B2
(45) **Date of Patent: *Oct. 27, 2026**

(54) COCHLEAR IMPLANT SYSTEM WITH ELECTRODE IMPEDANCE DIAGNOSTICS

(71) Applicant: ENVOY MEDICAL CORPORATION, White Bear Lake, MN (US)

(72) Inventor: Paul R. Mazanec, Ham Lake, MN (US)

(73) Assignee: ENVOY MEDICAL CORPORATION, White Bear Lake, MN (US)

( * ) Notice: Subject to any disclaimer, the term of this patent is extended or adjusted under 35 U.S.C. 154(b) by 131 days.

This patent is subject to a terminal disclaimer.

(21) Appl. No.: 18/535,801

(22) Filed: Dec. 11, 2023

(65) Prior Publication Data

US 2024/0108898 A1 Apr. 4, 2024

Related U.S. Application Data

(63) Continuation of application No. 17/222,034, filed on Apr. 5, 2021, now Pat. No. 11,865,339.

(51) Int. Cl.

*A61N 1/36* (2006.01)
*A61N 1/05* (2006.01)
*A61N 1/372* (2006.01)

(52) U.S. Cl.

CPC ....... *A61N 1/36038* (2017.08); *A61N 1/0541* (2013.01); *A61N 1/3614* (2017.08); *A61N 1/36142* (2013.01); *A61N 1/37211* (2013.01)

(58) Field of Classification Search

None

See application file for complete search history.

(56) References Cited

U.S. PATENT DOCUMENTS 2,827,041 A 3/1958 Pierson
4,400,590 A 8/1983 Michelson (Continued)

FOREIGN PATENT DOCUMENTS

CN 104394930 A 3/2015
CN 110086237 A 8/2019

(Continued)

OTHER PUBLICATIONS

International Patent Application No. PCT/US2022/023049, International Search Report and Written Opinion mailed Jul. 22, 2022, 14 pages.

*Primary Examiner* — Erica S Lee

(74) *Attorney, Agent, or Firm* — Fredrikson & Byron, P.A.

(57) ABSTRACT

Cochlear implant systems can comprise a cochlear implant system comprising a cochlear electrode, a stimulator in electrical communication with the cochlear electrode, a return electrode, and one or more controllers. The cochlear electrode can include a first contact electrode and the stimulator can include a first source element in electrical communication with the first contact electrode. The one or more controllers can be configured to cause the stimulator to emit a predetermined current from the first source element to the return electrode via a first current path and determine a first voltage at the first contact electrode and a second voltage at the return electrode. The one or more controllers can determine an impedance associated with the first current path and determine one or more stimulation parameters, such as a compliance voltage for sourcing a prescribed current, for the source element based on the determined impedance.

23 Claims, 9 Drawing Sheets

(56) References Cited

U.S. PATENT DOCUMENTS 4,495,384 A 1/1985 Scott et al.
4,532,930 A 8/1985 Crosby et al.
4,729,366 A 3/1988 Schaefer
4,850,962 A 7/1989 Schaefer
4,918,745 A 4/1990 Hutchison
5,540,095 A 7/1996 Sherman et al.
5,609,616 A 3/1997 Schulman et al.
5,755,742 A 5/1998 Schuelke et al.
5,762,583 A 6/1998 Adams et al.
6,195,585 B1 2/2001 Karunasiri et al.
6,212,431 B1 4/2001 Hahn et al.
6,259,951 B1 7/2001 Kuzma et al.
6,272,382 B1 8/2001 Faltys et al.
6,308,101 B1 10/2001 Faltys et al.
6,358,281 B1 3/2002 Berrang et al.
6,391,024 B1 5/2002 Sun et al.
6,556,870 B2 4/2003 Zierhofer et al.
7,225,028 B2 5/2007 Della et al.
7,319,906 B2 1/2008 Kuzma et al.
7,376,563 B2 5/2008 Leysieffer et al.
7,524,278 B2 4/2009 Madsen et al.
7,729,775 B1 6/2010 Saoji et al.
7,853,330 B2 12/2010 Bradley et al.
8,554,329 B1 10/2013 Mann et al.
8,626,308 B2 1/2014 Meskens
8,655,449 B2 2/2014 Haller et al.
8,954,158 B2 2/2015 Smith
9,036,824 B2 5/2015 Mazanec
9,061,140 B2 6/2015 Shi et al.
9,205,272 B2 12/2015 Suaning et al.
9,409,027 B2 8/2016 Markey et al.
9,504,076 B2 11/2016 El-Hoiydi et al.
9,539,430 B2 1/2017 Mishra et al.
9,693,155 B2 6/2017 Meister et al.
9,700,730 B2 7/2017 Carbunaru et al.
9,716,952 B2 7/2017 Mauger
9,769,558 B2 9/2017 Chandramohan et al.
9,999,770 B2 6/2018 Walraevens et al.
10,187,792 B2 1/2019 Meskens
10,220,201 B2 3/2019 Mauch et al.
10,306,472 B2 5/2019 Battiwalla et al.
10,357,656 B2 7/2019 Heasman
10,560,789 B2 2/2020 Koka et al.
10,561,335 B2 2/2020 Nielsen et al.
10,668,284 B2 6/2020 Koka et al.
10,713,936 B2 7/2020 Banna et al.
11,083,391 B2 8/2021 Carter
11,317,842 B2 5/2022 Koka et al.
11,324,958 B2 5/2022 Anderson et al.
11,471,689 B2 10/2022 Mazanec
11,865,339 B2 * 1/2024 Mazanec ............ A61N 1/36038
2002/0015506 A1 2/2002 Aceti et al.
2002/0039425 A1 4/2002 Burnett et al.
2002/0099421 A1 7/2002 Goldsmith et al.
2003/0114899 A1 6/2003 Woods et al.
2004/0230254 A1 11/2004 Harrison et al.
2005/0033384 A1 2/2005 Sacha
2005/0197677 A1 9/2005 Stevenson
2006/0122664 A1 6/2006 Sacha et al.
2006/0183965 A1 8/2006 Kasic et al.
2007/0055322 A1 3/2007 Forsberg et al.
2008/0195179 A1 8/2008 Quick
2008/0300658 A1 12/2008 Meskens
2009/0018616 A1 1/2009 Quick et al.
2009/0082831 A1 3/2009 Paul et al.
2009/0171421 A1 7/2009 Atalar et al.
2009/0177247 A1 7/2009 Neal et al.
2009/0187233 A1 7/2009 Stracener
2009/0192565 A1 7/2009 Lee et al.
2010/0010582 A1 1/2010 Carbunaru et al.
2010/0030012 A1 2/2010 Meskens
2010/0042183 A1 2/2010 Beck
2010/0290651 A1 11/2010 Grayden et al.
2010/0317913 A1 12/2010 Conn et al.
2011/0077698 A1 3/2011 Tsampazis et al.
2011/0082521 A1 4/2011 Botros et al.
2011/0098785 A1 4/2011 Mishra
2011/0116669 A1 5/2011 Karunasiri
2011/0137180 A1 6/2011 Johnson et al.
2011/0144719 A1 6/2011 Perkins et al.
2011/0160808 A1 6/2011 Lyden et al.
2011/0280426 A1 11/2011 Bachler
2011/0295331 A1 12/2011 Wells et al.
2012/0063610 A1 3/2012 Kaulberg et al.
2012/0215285 A1 8/2012 Tahmasian et al.
2012/0277835 A1 11/2012 Della et al.
2013/0018216 A1 1/2013 Beckerle et al.
2013/0023953 A1 1/2013 Den
2013/0023960 A1 1/2013 Stafford
2013/0073002 A1 3/2013 Nygard et al.
2013/0193914 A1 8/2013 Gaddam et al.
2013/0197613 A1 8/2013 Kelly et al.
2013/0223664 A1 8/2013 Meskens et al.
2013/0238048 A1 9/2013 Almendinger et al.
2013/0238055 A1 9/2013 Marnfeldt et al.
2013/0268025 A1 10/2013 Ranu
2013/0278226 A1 10/2013 Cong et al.
2013/0317584 A1 11/2013 Stevenson et al.
2014/0058482 A1 2/2014 Gupta et al.
2014/0070761 A1 3/2014 Labbe et al.
2014/0155947 A1 6/2014 Kroll et al.
2014/0247954 A1 9/2014 Hall et al.
2014/0270211 A1 9/2014 Solum et al.
2014/0275730 A1 9/2014 Lievens et al.
2014/0309712 A1 10/2014 Masaki et al.
2014/0350652 A1 11/2014 Suwito
2015/0125012 A1 5/2015 Sabin
2015/0174416 A1 6/2015 Angara et al.
2015/0224312 A1 8/2015 Platz et al.
2015/0256945 A1 9/2015 Mazanec
2015/0374988 A1 12/2015 Laudanski
2015/0375003 A1 12/2015 Meskens
2016/0001077 A1 1/2016 Pontoppidan et al.
2016/0050500 A1 2/2016 Liao et al.
2016/0144177 A1 5/2016 Saoji et al.
2016/0144184 A1 5/2016 Marnfeldt
2016/0213925 A1 7/2016 Karunasiri
2016/0227333 A1 8/2016 Babico
2016/0287870 A1 10/2016 Yip et al.
2017/0043162 A1 2/2017 Lopez-Poveda
2017/0077938 A1 3/2017 Heubi
2017/0094396 A1 3/2017 Chandramohan et al.
2017/0161449 A1 6/2017 Meskens
2017/0197079 A1 * 7/2017 Illegems ............ A61N 1/37211
2017/0259072 A1 9/2017 Newham et al.
2017/0296810 A1 10/2017 Thakur et al.
2017/0360364 A1 12/2017 Heasman et al.
2018/0028811 A1 2/2018 Van Gerwen et al.
2018/0028827 A1 2/2018 Schilling et al.
2018/0041848 A1 2/2018 Nielsen et al.
2018/0050197 A1 2/2018 Mazanec et al.
2018/0050198 A1 2/2018 Mazanec et al.
2018/0050203 A1 2/2018 Mazanec et al.
2018/0056058 A1 3/2018 Heasman et al.
2018/0059870 A1 3/2018 Krah
2018/0264269 A1 9/2018 Meadows
2018/0317027 A1 11/2018 Bolner et al.
2018/0333577 A1 11/2018 Nygard et al.
2018/0361151 A1 12/2018 Ridler et al.
2019/0045308 A1 2/2019 Chen et al.
2019/0046116 A1 2/2019 Shah et al.
2019/0190296 A1 6/2019 Paralikar et al.
2019/0217101 A1 * 7/2019 Shi ...................... A61N 1/0534
2019/0231203 A1 8/2019 Harczos
2019/0344073 A1 11/2019 Baker et al.
2019/0358450 A1 11/2019 Lo et al.
2020/0054877 A1 2/2020 Calixto et al.
2020/0238075 A1 7/2020 Mazanec et al.
2020/0261720 A1 * 8/2020 Danitz .................. A61N 1/375
2020/0269034 A1 8/2020 Mazanec et al.
2020/0269035 A1 8/2020 Mazanec et al.
2020/0269047 A1 8/2020 Mazanec et al.
2020/0269048 A1 8/2020 Mazanec et al.
2020/0269057 A1 8/2020 Mazanec et al.

(56) References Cited

U.S. PATENT DOCUMENTS

| | | | |
|---|---|---|---|
| 2020/0269058 | A1 | 8/2020 | Mazanec et al. |
| 2021/0084417 | A1 | 3/2021 | Bagazov et al. |
| 2021/0121707 | A1 | 4/2021 | Fried et al. |
| 2021/0135704 | A1 | 5/2021 | El-Hoiydi et al. |
| 2021/0187293 | A1 | 6/2021 | Friedling |
| 2021/0361194 | A1 | 11/2021 | Arab et al. |
| 2022/0070594 | A1 | 3/2022 | Mazanec |
| 2022/0168569 | A1 | 6/2022 | Mazanec |
| 2022/0168570 | A1 | 6/2022 | Mazanec |
| 2022/0168581 | A1 | 6/2022 | Mazanec |
| 2022/0203104 | A1 | 6/2022 | Hernandez et al. |
| 2022/0339445 | A1 | 10/2022 | Litvak et al. |
| 2023/0008440 | A1* | 1/2023 | Ackermann ......... A61N 1/0404 |

FOREIGN PATENT DOCUMENTS

| | | | |
|---|---|---|---|
| DE | 4419070 | A1 | 12/1994 |
| DE | 60107062 | T2 | 12/2004 |
| DE | 102013214049 | B4 | 3/2015 |
| EP | 1043914 | A2 | 10/2000 |
| EP | 1683544 | B1 | 11/2010 |
| EP | 2884766 | B1 | 2/2018 |
| EP | 3120579 | B1 | 2/2020 |
| JP | 2016024111 | A | 2/2016 |
| TW | 201142830 | A | 12/2011 |
| WO | 2007137032 | A2 | 11/2007 |
| WO | 2010056768 | A1 | 5/2010 |
| WO | 2014037888 | A1 | 3/2014 |
| WO | 2014054215 | A1 | 4/2014 |
| WO | 2015077773 | A1 | 5/2015 |
| WO | 2016122606 | A1 | 8/2016 |
| WO | 2017100866 | A1 | 6/2017 |
| WO | 2018035329 | A1 | 2/2018 |
| WO | 2018144732 | A1 | 8/2018 |
| WO | 2020172500 | A1 | 8/2020 |

* cited by examiner

COCHLEAR IMPLANT SYSTEM WITH ELECTRODE IMPEDANCE DIAGNOSTICS

CROSS-REFERENCE

This application is a continuation of U.S. patent application Ser. No. 17/222,034, filed on Apr. 5, 2021, the entire contents of which is incorporated herein by reference.

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

Cochlear implants may stimulate the cochlear tissue using implanted electrical components which generate and send electrical signals. The electrical components can be powered using an implanted battery which may need to be recharged or replaced when it runs out of electrical charge. The electrical components can require a minimum amount of voltage and/or current to operate safely when generating and sending electrical signals. If the voltage and/or current of the electrical components does not meet the minimum requirements, charge may accumulate within the tissue. Charge accumulation may cause damage to the cochlear tissue and/or implanted components.

SUMMARY

Some aspects of the disclosure are generally directed toward cochlear implant systems. In some embodiments, a cochlear implant system can include a cochlear electrode comprising a first contact electrode and a second contact electrode. The cochlear implant system can further include a stimulator in electrical communication with the cochlear electrode. The stimulator can include a first source element in electrical communication with the first contact electrode and a second source element in electrical communication with the second contact electrode. The stimulator can further comprise a return electrode and a controller in electrical communication with the stimulator. In some embodiments, the controller is configured to apply an initial compliance voltage to the first source element and cause the stimulator to emit a first predetermined electrical current from the first source element to the return electrode via a first current path. The controller can further be configured to determine a first voltage corresponding to a voltage at the first contact electrode relative to a reference voltage. Additionally, the controller can be configured to determine a second voltage corresponding to a voltage at the return electrode relative to the reference voltage, the controller can also be configured to determine a first impedance associated with the first current path based on the determined first voltage, the determined second voltage and the predetermined electrical current emitted from the first source element. In some embodiments, the controller is also configured to determine a first compliance voltage for the first source element based on the determined first impedance and a first prescribed current for the first source element. If the determined first compliance voltage is sufficiently different from the initial compliance voltage, the controller can further be configured to adjust the operation of the first source element.

Some aspects of the disclosure are generally directed toward methods of adjusting operation of a cochlear implant system. In some embodiments, the method includes providing an initial compliance voltage to a first source element and causing a stimulator to emit a first predetermined electrical current from the first source element to a return electrode via a first current path. The method can also include determining a first voltage corresponding to a voltage at the first contact electrode relative to a reference voltage. Further, the method can include determining a second voltage corresponding to a voltage at the return electrode relative to the reference voltage. The method additionally includes determining a first impedance associated with the first current path based on the determined first voltage, the determined second voltage, and the first predetermined electrical current emitted from the first source element. The method can also include determining a first compliance voltage for the first source element based on the determined first impedance and a first prescribed current for the first source element. If the determined first compliance voltage is different from the initial compliance voltage, the method can also include adjusting the operation of the first source element.

DETAILED DESCRIPTION

Figure 1:
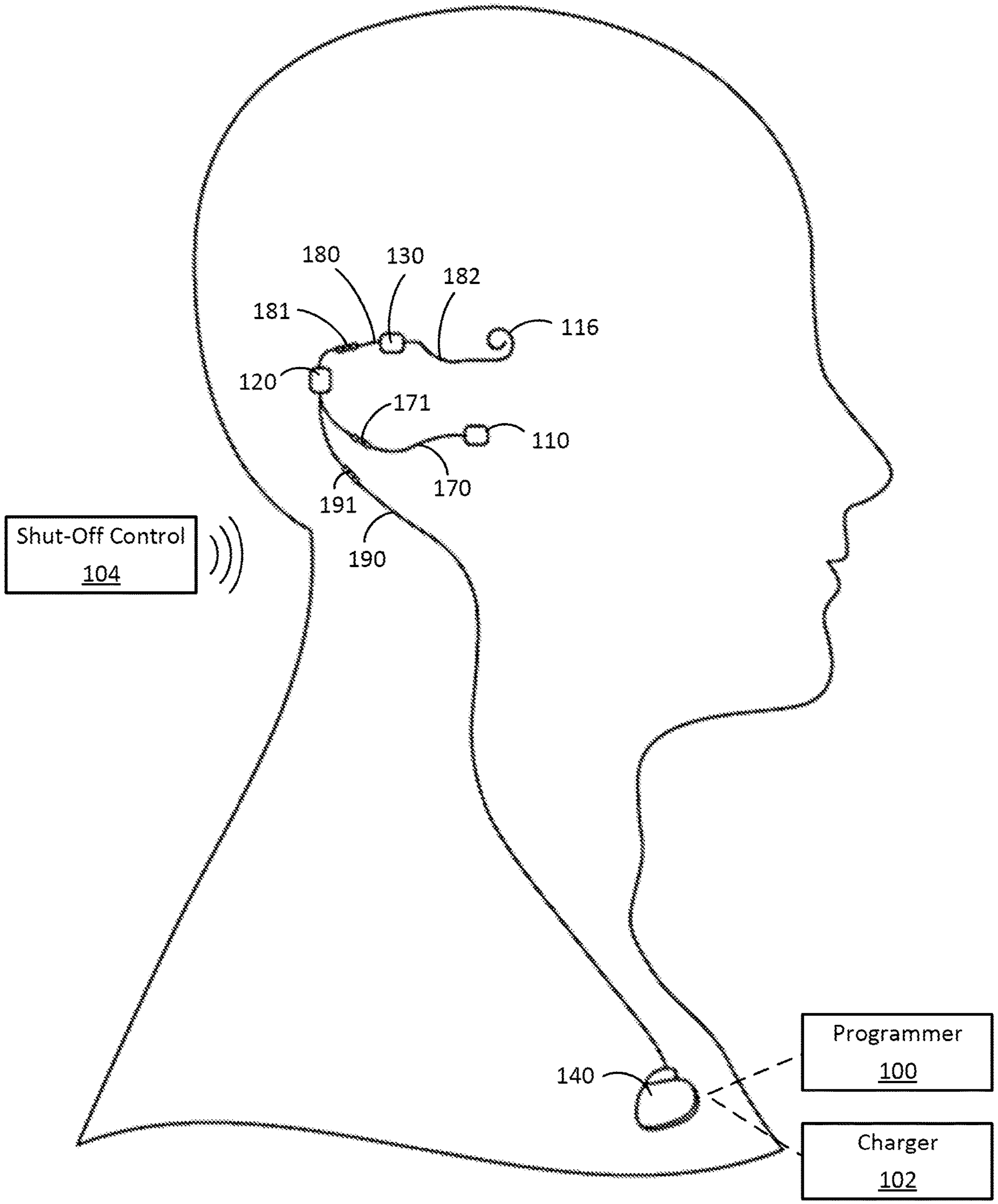
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 1/20 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

In various examples, the signal processor 120 can comprise any variety of components, for example, digital and/or analog processing components. In some embodiments, signal processor 120 comprises a digital signal processor, one or more microprocessors, microcontrollers, application specific integrated circuits (ASICs) or the like. Supporting circuitry for one or more such components can also be included as a part of the signal processor. In some embodiments, the signal processor can include or otherwise communicate with a memory containing programming for operating one or more components. Additionally or alternatively, in some embodiments, the signal processor can include one or more additional components. For example, in some embodiments, signal processor can include an embedded microphone or other sensor configured to detect incoming sound waves.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
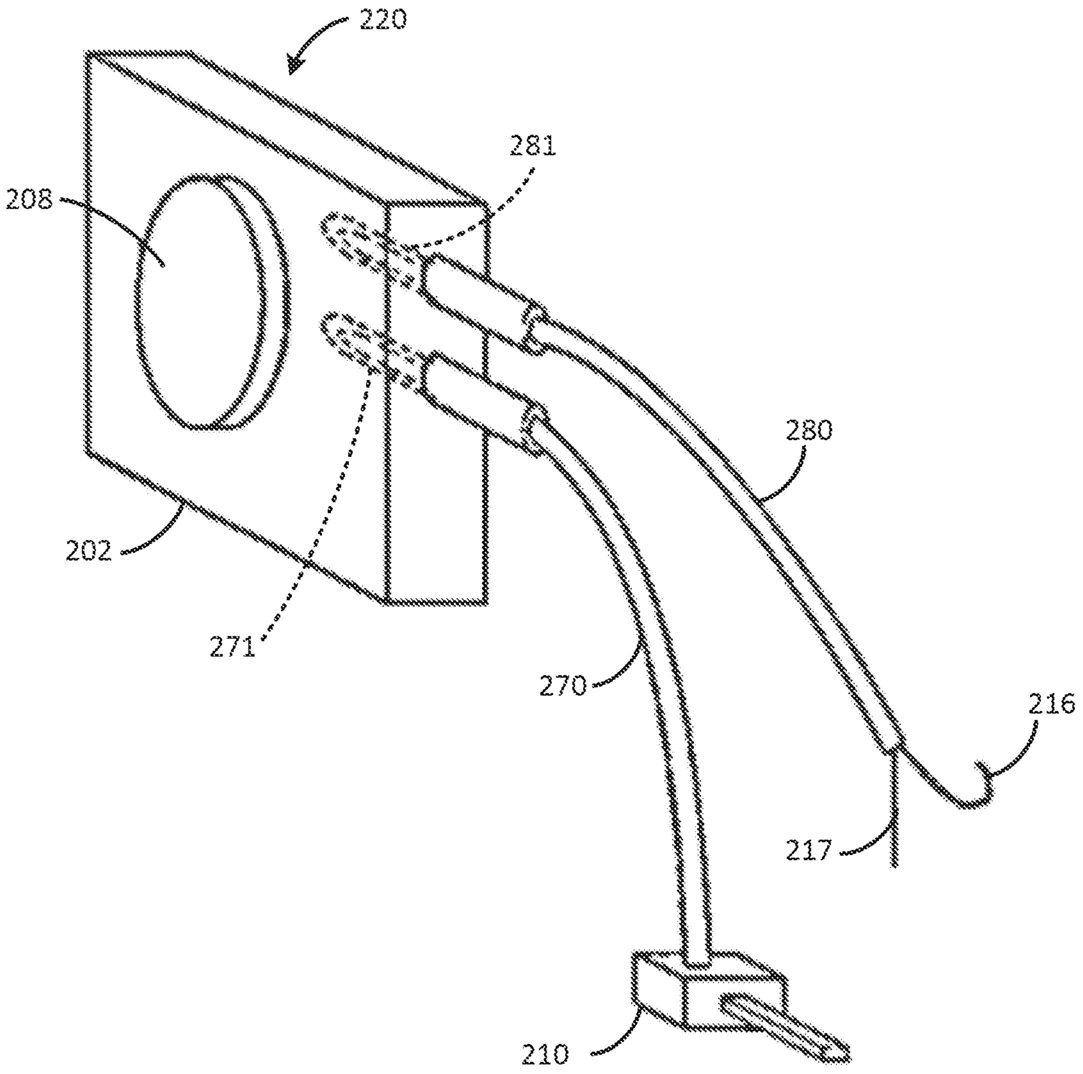
FIG. 2 shows an embodiment of a fully implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3:
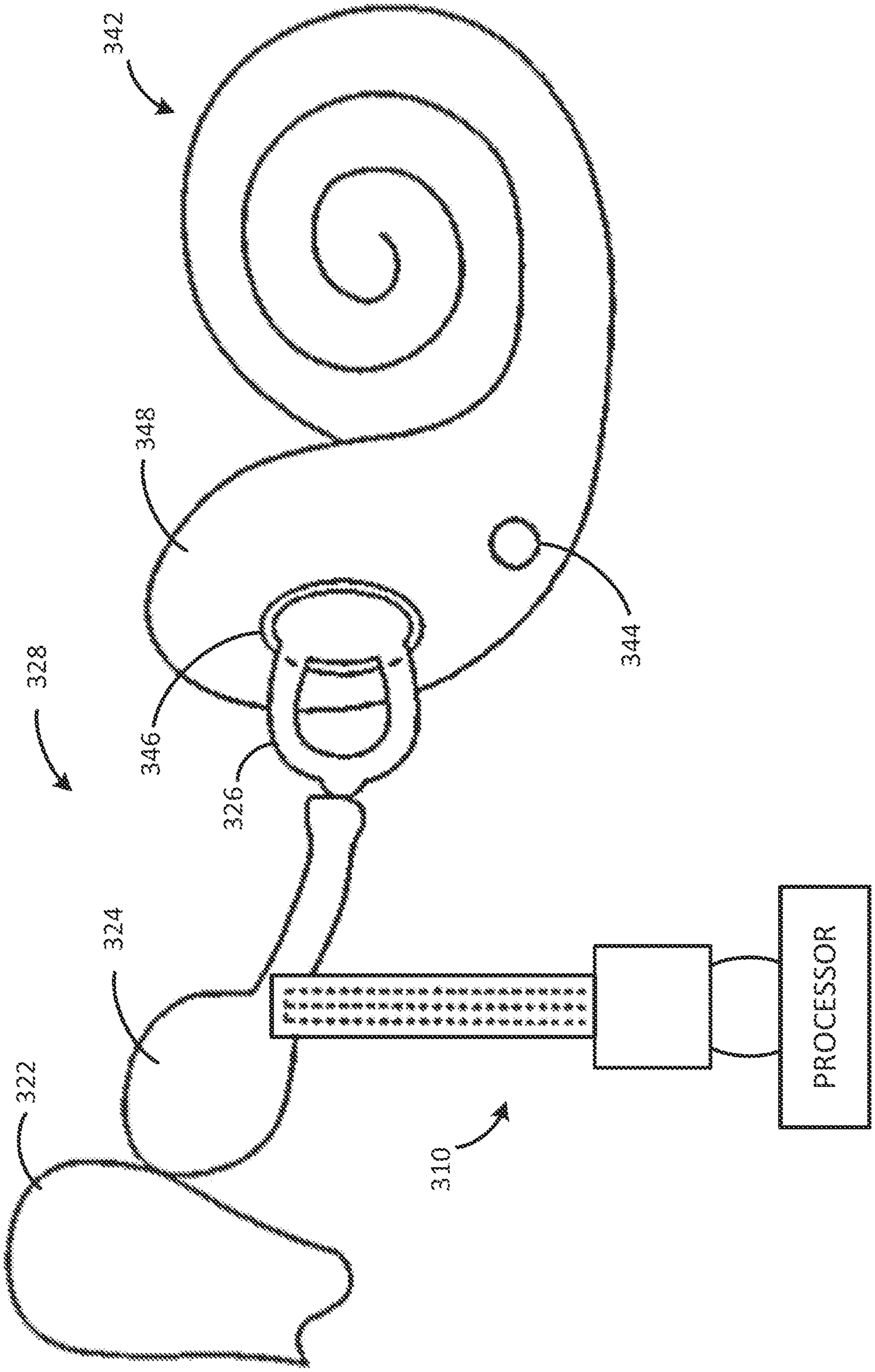
FIG. 3 illustrates an embodiments of an exemplary middle ear sensor for use in conjunction with anatomical features of a patient.

FIG. 3 illustrates embodiments of an exemplary middle ear sensor for use in conjunction with anatomical features of a patient. Referring to FIG. 3, an embodiment of the sensor 310 of a fully-implantable cochlear implant is shown. Also shown are portions of the subject's anatomy, which includes, if the subject is anatomically normal, at least the malleus 322, incus 324, and stapes 326 of the middle ear 328, and the cochlea 348, oval window 346, and round window 344 of the inner ear 342. Here, the sensor 310 is touching the incus 324. The sensor 310 can include a sensor such as described in U.S. Patent Publication No. 2013/0018216, which is incorporated by reference. Further, although not shown in a drawing, the sensor 310 may be in operative contact with the tympanic membrane or the stapes, or any combination of the tympanic membrane, malleus 322, incus 324, or stapes 326.

FIG. 3 illustrates an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function. Additionally or alternatively, systems can include other types of sensors, such as inner ear sensors. Some example configurations of such systems and other sensor arrangements are described in PCT patent application No. PCT/US20/19166, filed Feb. 21, 2020, which is assigned to the assignee of the instant application and is incorporated by reference.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140.

In some embodiments, the implantable battery and/or communication module 140 can communicate with one or more external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and battery charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. Example detachable connectors are described in PCT patent application No. PCT/US20/19166, which is incorporated by reference. For example, with reference to FIG. 1, in some embodiments, lead 170 can include a first lead extending from the middle ear sensor 110 having one of a male or a female connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120. For example, in an exemplary embodiment, the signal processor 120 can include a female connector integrated into a housing of the signal processor 120. Lead 170 can extend fully from the middle ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a modular signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
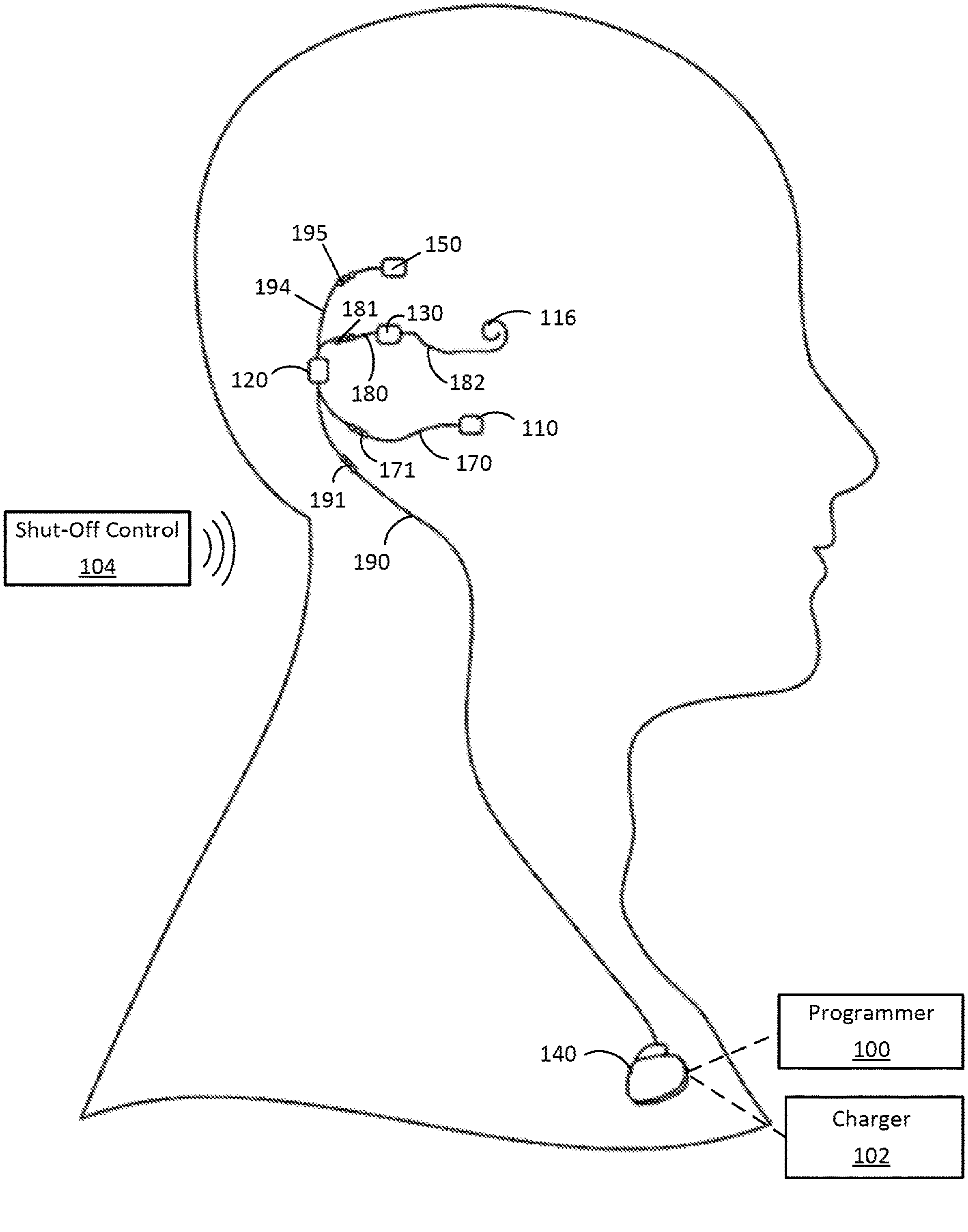
FIG. 4 is a schematic diagram illustrating an exemplary implantable system including an acoustic stimulator.

FIG. 4 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic stimulator of FIG. 4 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic stimulator such as shown in FIG. 4 can operate in the same way as systems described elsewhere herein employing an electrical stimulator and cochlear electrode only substituting electrical stimulation for acoustic stimulation.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

Additionally or alternatively, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function. Additionally or alternatively, systems can include a middle ear sensor as an input source, wherein the middle ear sensor is configured to detect stimuli (e.g., pressure signals) from the wearer's inner ear (e.g., within the cochlear tissue).

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

In some examples, implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component).

Figure 5A:
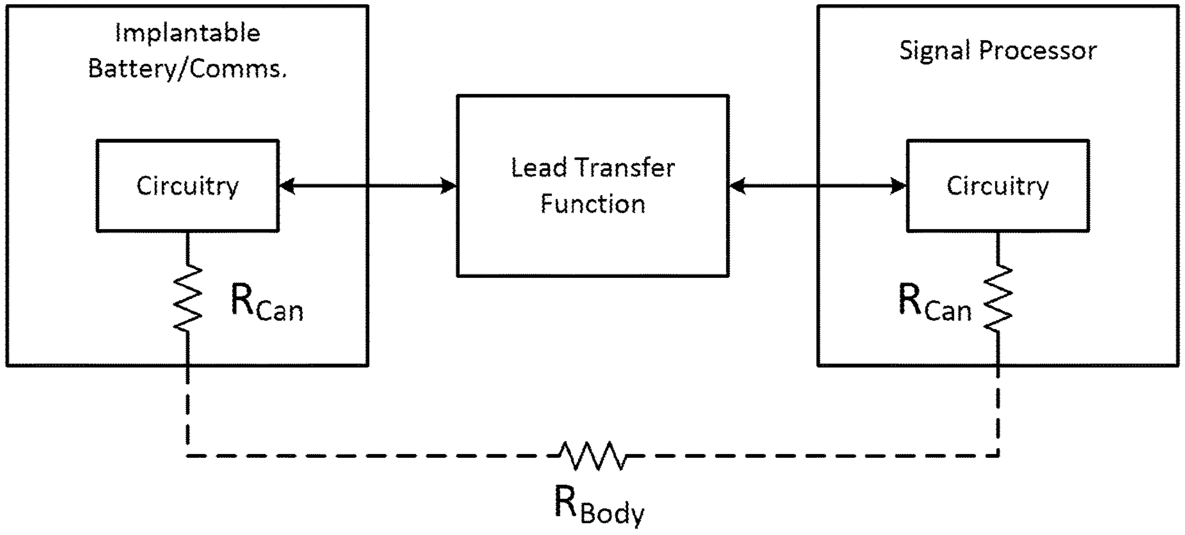
FIG. 5A is a high-level electrical schematic showing communication between the implantable battery and/or communication module and the signal processor.

FIG. 5A is a high-level electrical schematic showing communication between the implantable battery and/or communication module and the signal processor. In the illustrated embodiment, the implantable battery and/or communication module includes circuitry in communication with circuitry in the signal processor. Communication between the circuitry in the implantable battery and/or communication module and the signal processor can be facilitated by a lead (190), represented by the lead transfer function. The lead transfer function can include, for example, parasitic resistances and capacitances between the leads connecting the implantable battery and/or communication module and the signal processor and the patient's body and/or between two or more conductors that make up the lead (e.g., 191). Signals communicated from the circuitry of the implantable battery and/or communication module to the circuitry in the signal processor can include electrical power provided to operate and/or stimulate system components (e.g., the middle ear sensor, signal processor, electrical and/or acoustic stimulator, and/or cochlear electrode) and/or data (e.g., processing data regarding the transfer function of the signal processor).

Various systems and methods can be employed provide communication between system components. Some examples of possible communication techniques are described in PCT patent application No. PCT/US20/19166, which is incorporated by reference. In some examples, data can be communicated to the implantable battery and/or communication module from an external component, such as a programmer as shown in FIG. 1. In an exemplary process, a programmer, such as a clinician's computer, can be used to communicate with a patient's fully implanted system via the implantable battery and/or communication module, which can communicate information to other system components, such as via lead 190.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE MEASUREMENT FOR HEARING AID, which is assigned to the assignee of the instant application, the relevant portions of which are incorporated by reference herein.

As discussed elsewhere herein, the body of the patient provides an electrical path between system components, such as the "can" of the implantable battery and/or communication module and the "can" of the signal processor. This path is represented in FIG. 5A by the flow path through $R_{Body}$. Thus, the patient's body can provide undesirable signal paths which can negatively impact communication between components. To address this, in some embodiments, operating circuitry in each component can be substantially isolated from the component "can" and thus the patient's body. For example, as shown, resistance Roan is positioned between the circuitry and the "can" of both the implantable battery and/or communication module and the signal processor.

While being shown as $R_{Can}$ in each of the implantable battery and/or communication module and the signal processor, it will be appreciated that the actual value of the resistance between the circuitry and respective "can" of different elements is not necessarily equal. Additionally, $R_{Can}$ need not include purely a resistance, but can include other components, such as one or more capacitors, inductors, and the like. That is, $R_{Can}$ can represent an insulating circuit including any variety of components that act to increase the impedance between circuitry within a component and the "can" of the component. Thus, $R_{Can}$ can represent an impedance between the operating circuitry of a component and the respective "can" and the patient's tissue. Isolating the circuitry from the "can" and the patient's body acts to similarly isolate the circuitry from the "can" of other components, allowing each component to operate with reference to a substantially isolated component ground. This can eliminate undesired communication and interference between system components and/or between system components and the patient's body.

Figure 5B:
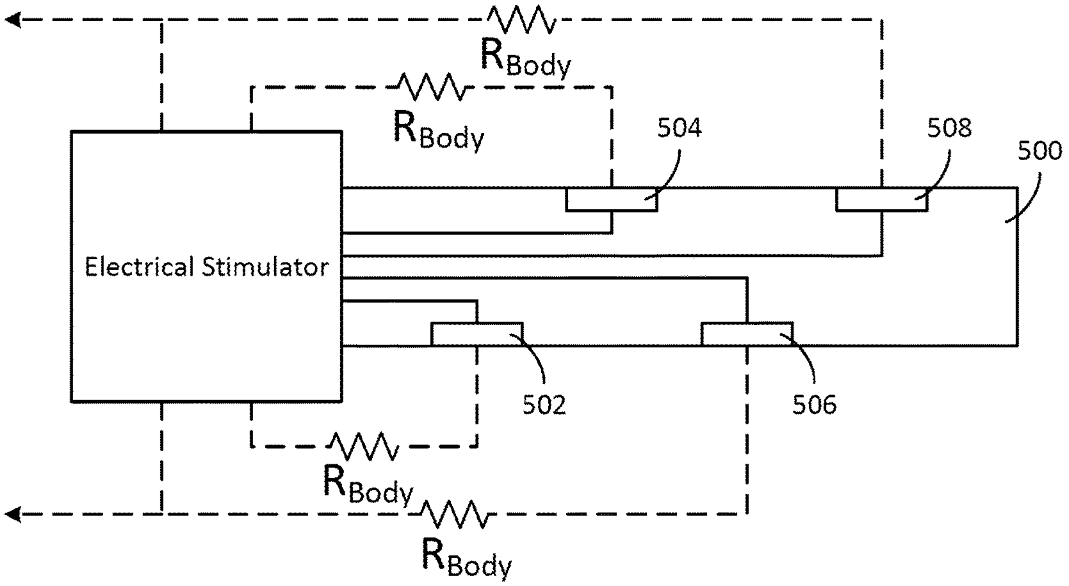
FIG. 5B illustrates an exemplary schematic diagram illustrating a cochlear electrode having a plurality of contact electrodes and fixedly or detachably connected to an electrical stimulator.

For example, as described elsewhere herein, in some examples, an electrical stimulator can provide an electrical stimulus to one or more contact electrodes on a cochlear electrode implanted in a patient's cochlear tissue. FIG. 5B illustrates an exemplary schematic diagram illustrating a cochlear electrode having a plurality of contact electrodes and fixedly or detachably connected to an electrical stimulator. As shown, the cochlear electrode 500 has four contact electrodes 502, 504, 506, and 508, though it will be appreciated that any number of contact electrodes is possible. As described elsewhere herein, the electrical stimulator can provide electrical signals to one or more such contact electrodes in response to an output from the signal processor according to the transfer function thereof and a received input signal.

Because each contact electrode 502-508 is in contact with the patient's cochlear tissue, each is separated from the "can" of the electrical stimulator (as well as the "cans" of other system components) via the impedance of the patient's tissue, shown as $R_{Body}$. Thus, if the circuitry within various system components did not have sufficiently high impedance (e.g., $R_{Can}$) to the component "can", electrical signals may stimulate undesired regions of the patient's cochlear tissue. For instance, stimulation intended for a particular contact electrode (e.g., 502) may lead to undesired stimulation of other contact electrodes (e.g., 504, 506, 508), reducing the overall efficacy of the system Minimizing the conductive paths between system components (e.g., to the contact electrodes of a cochlear electrode) due to the patient's body, such as by incorporating impedances between component circuitry and the corresponding "can" via $R_{Can}$, can therefore improve the ability to apply an electrical stimulus to only a desired portion of the patient's body.

It will be appreciated that the term $R_{Body}$ is used herein to generally represent the resistance and/or impedance of the patient's tissue between various components and does not refer to a specific value. Moreover, each depiction or $R_{Body}$ in the figures does not necessarily represent the same value of resistance and/or impedance as the others.

Figure 6A:
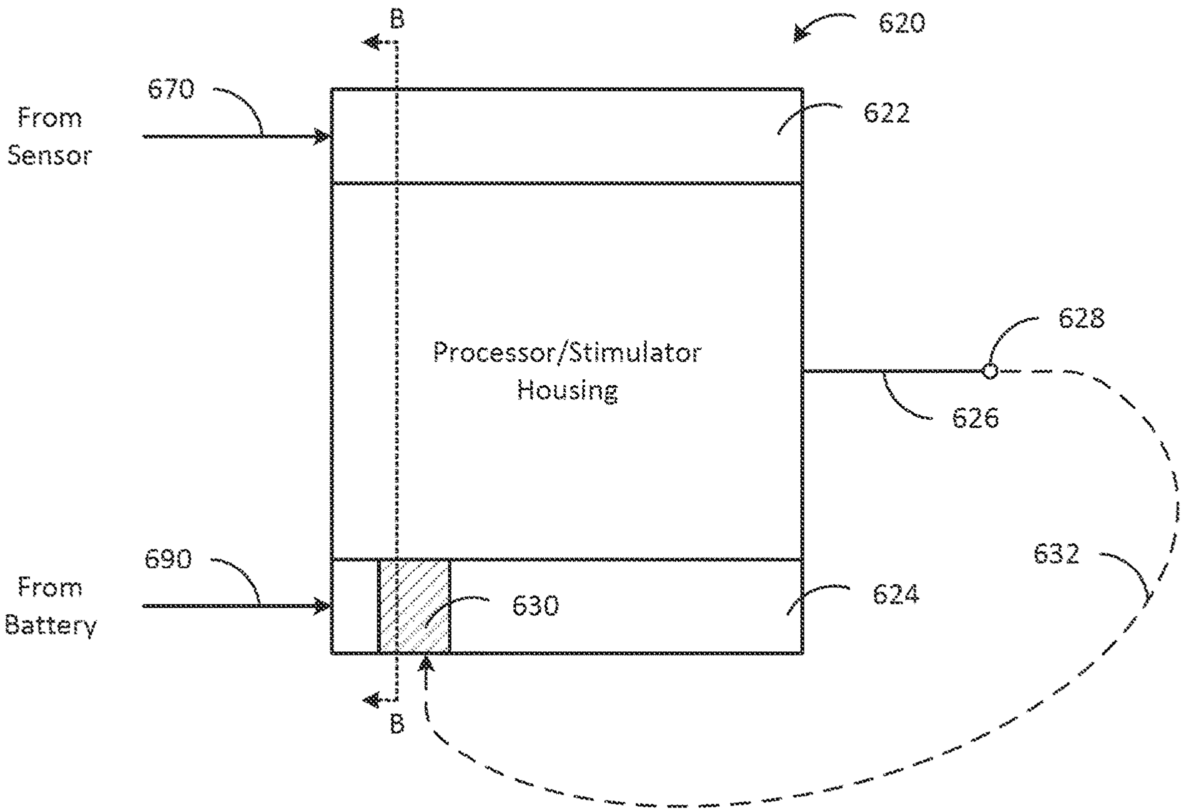
FIG. 6A shows an exemplary schematic illustration of processor and stimulator combined into a single housing.

While shown in several embodiments (e.g., FIGS. 1 and 4) as being separate components connected by a lead (e.g., lead 180), in some examples, the processor (e.g., 120) and the stimulator (e.g., 130) can be integrated into a single component, for example, within a hermetically sealed housing. FIG. 6A shows an exemplary schematic illustration of processor and stimulator combined into a single housing. In the example of FIG. 6A, the processor/stimulator 620 receives signal inputs from the sensor (e.g., a middle ear sensor) via lead 670 and power from a battery (e.g., the implantable battery and/or communication module) via lead 690. The processor/stimulator 620 can include headers 622, 624 for receiving leads 670, 690, respectively.

The processor/stimulator 620 can be configured to receive an input signal from the sensor, process the received input signal according to a transfer function, and output a stimulation signal via electrode 626. Electrode 626 can include one or more contact electrodes (e.g., 628) in contact with a wearer's cochlear tissue to provide electrical stimulation thereto, for example, as described with respect to FIG. 5B.

The processor/stimulator 620 of FIG. 6 includes a return electrode 630 for providing a return path (e.g., 632) for electrical stimulation emitted from electrode 626. The return electrode 630 can be electrically coupled to a ground portion of circuitry within the processor/stimulator 620 to complete a circuit comprising circuitry within the processor/stimulator 620, the electrode 626, the wearer's cochlear tissue, and ground. In some examples, the return electrode 630 comprises an electrically conductive material in electrical communication with circuitry inside the processor/stimulator 620, while the rest of the housing of the processor/stimulator 620 is generally not electrically coupled to internal circuitry.

In some embodiments, the return electrode 630 and the housing of the processor/stimulator 620 comprise electrically conductive materials. For instance, in some examples, the housing comprises titanium while the return electrode 630 comprises platinum or a platinum alloy. Header 624 can generally include a non-conductive biocompatible material, such as a biocompatible polymer. The non-conductive header 624 can provide isolation between the return electrode 630 and the conductive housing of the processor/stimulator 620.

While shown in FIG. 6A as being positioned in the power header 624 of the processor/stimulator 620, in general, the return electrode 630 can be positioned anywhere on the exterior surface of the processor/stimulator 620. In some examples, one or more redundant return electrodes can be included, for example, at or near the interface of the housing and the electrode 626. In some examples, a return electrode can be positioned on a proximal end of the electrode 626 itself. In some embodiments having a plurality of return electrodes (e.g., return electrode 630 and a return electrode on the proximal end of electrode 626), a switch can be used to select which return electrode is used. Additionally or alternatively, a plurality of return electrodes can be used simultaneously.

Figure 6B:
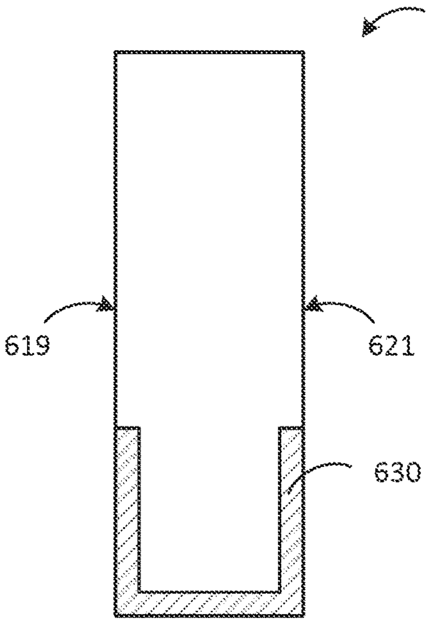
FIG. 6B shows a simplified cross-sectional view of the processor/stimulator shown in FIG. 6A taken along lines B-B.

FIG. 6B shows a simplified cross-sectional view of the processor/stimulator shown in FIG. 6A taken along lines B-B. As shown in FIG. 6B, processor/stimulator 620 includes a housing having a first side 619 and a second side 621 and a return electrode 630 embedded in the housing. Return electrode 630 can comprise a conductive material suitable for contact with a wearer's tissue, such as platinum. In the illustrated example, the return electrode 630 wraps around to both sides of the housing of the processor/stimulator 620 so that the return electrode 630 is coupled to the outer surface of the housing on the first side 619 and the second side 621.

This can facilitate implanting onto either side of a wearer's anatomy, since in some cases, only one side of the processor/stimulator electrically contacts conductive tissue of the wearer while the other side contacts, for instance, the skull of the wearer, and does not easily provide the return path (e.g., 632). Thus, a single processor/stimulator design can be implanted in either side of a wearer's anatomy while providing an adequate return path via a return electrode 630.

In various examples, the return electrode 630 can extend around a perimeter edge of the processor/stimulator 620, as shown in FIG. 6B. In other examples, the return electrode 630 can include sections on either side of the housing and can be connected to one another internally within the housing rather than via a wrap-around contact. Additionally, while shown as being embedded in the housing of the processor/stimulator 620, in some examples, return electrode 630 can protrude outwardly from the housing. Return electrode 630 can generally be any of a variety of shapes and sizes while including an electrical contact section on opposing sides of the housing to provide usability on either side of a wearer's anatomy. In other embodiments, return electrode can be positioned only one side of the housing for a customized right-side or left-side implementation.

As described elsewhere herein, in various embodiments of a cochlear implant system, a processor generally receives an input signal, processes the signal, and generates a stimulation signal for output to a stimulator. A stimulator can provide electrical stimuli to cochlear tissue of a wearer of the cochlear implant via a cochlear electrode comprising one or more contact electrodes can apply. The stimulator can be configured to deliver a specific amount of charge to a wearer's cochlear tissue according to the received stimulation signal. The stimulator can include a return electrode which can provide a return path for the electrical stimuli, completing a circuit which includes the stimulator, the cochlear electrode, the wearer's tissue, and the return electrode.

It can be desirable to limit the electrical power applied to the components of the cochlear implant as in some embodiments, the cochlear implant is powered from a limited power supply (e.g., one or more implanted batteries or other energy storage element that eventually requires recharging). In such embodiments, limiting the electrical power applied to components can increase the amount of time the cochlear implant can be operational on the limited power supply before recharging is required. However, in some embodiments, the power provided to the components of the cochlear implant needs to be high enough as to ensure proper operation of such components. For instance, in some embodiments, source elements which do not receive enough voltage and/or current can cause unsafe conditions such as charge accumulation in a wearer's cochlear tissue. In such embodiments, precisely controlling the voltage applied to one or more source elements configured to source or sink current to or from a wearer's tissue and/or the current sourced or sunk by such source elements can optimize power consumption and increase operational time of a cochlear implant while maintaining proper operation of the cochlear implant.

Figure 7:
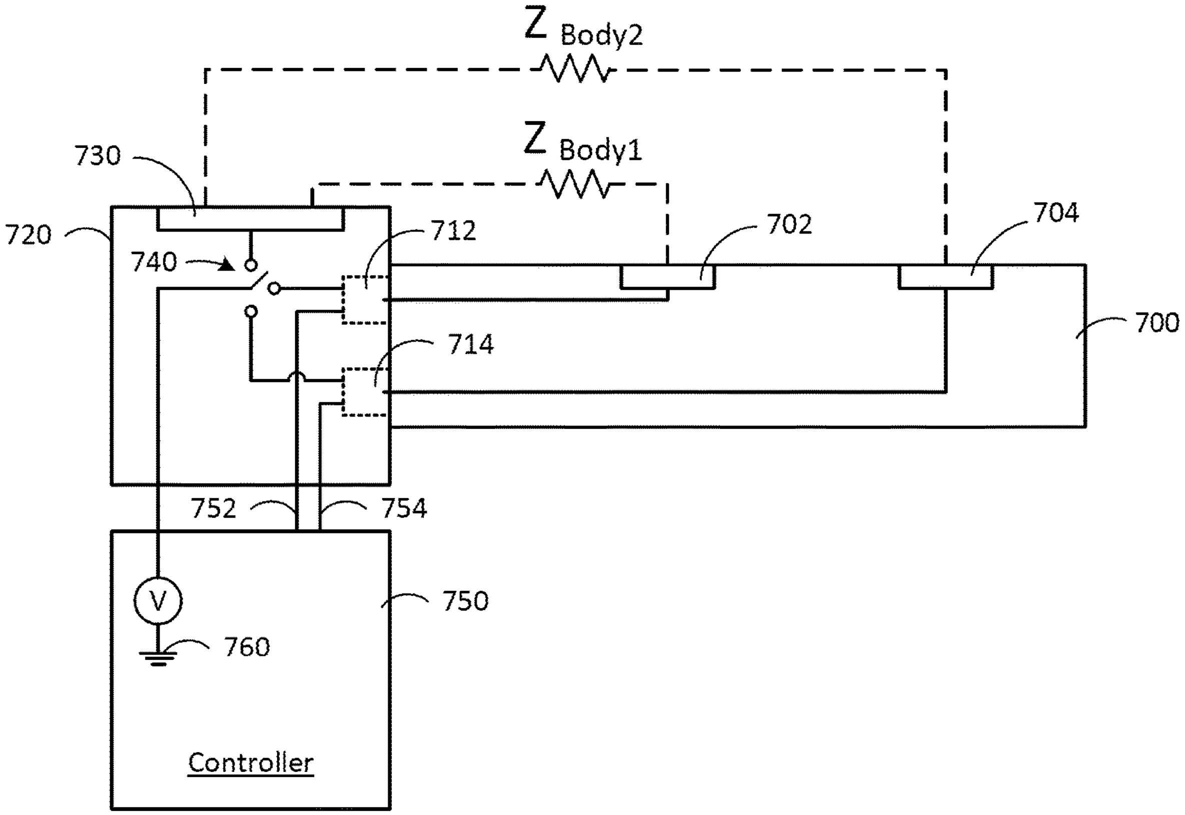
FIG. 7 is an electrical schematic of an example cochlear implant system.

FIG. 7 is an electrical schematic of an example cochlear implant system. The system includes a cochlear electrode 700 comprising a first contact electrode 702 and a second contact electrode 704. The system further includes a stimulator 720 which comprises a first source element 712 and a second source element 714 which are in electrical communication with the first contact electrode 702 and the second contact electrode 704, respectively. Source elements 712, 714 can be configured to receive a signal corresponding to an amount of current to be sourced from/sunk by the contact electrodes 702, 704 and source/sink such current accordingly. The stimulator 720 of FIG. 7 also includes a return electrode 730 and a switch 740. Switch 740 can be any appropriate component configured to provide electrical energy to a selectable location, such as a mechanical switch, electrical switch, or the like. As shown in the example of FIG. 7, the first contact electrode 702 and the second contact electrode 704 are in communication with the return electrode 730 through a wearer's cochlear tissue having current paths with impedances $Z_{Body1}$ and $Z_{Body2}$, respectively.

In the example of FIG. 7, a controller 750 is in communication with the first source element 712 and the second source element 714 of the stimulator 720 via connections 752/854, as well as a reference voltage 760 (e.g., a system ground). Controller 750 can comprise any variety of components configured to execute various processes described herein, for example, digital and/or analog processing components. In some embodiments, controller comprises a digital signal processor, one or more microprocessors, microcontrollers, application specific integrated circuits (ASICs) or the like. Supporting circuitry for one or more such components can also be included as a part of the controller. In some embodiments, the controller can include or otherwise communicate with a memory containing programming for operating one or more components.

In some embodiments, controller 750 comprises the signal processor (e.g., 120) in communication with the stimulator 720. In some embodiments, the controller 750 is the signal processor or is included as a part of the signal processor. In some examples, the controller 750 and stimulator 720 are included in a common housing, for example, similar to as shown in the examples of FIGS. 6A and 6B wherein the signal processor and stimulator are included in a common housing.

In some examples, the first source element 712 and the second source element 714 can include a current source and/or a current sink. As a current source, the first source element 712 can provide (e.g., source) a current to the first contact electrode 702 and the and the second source element 714 can provide (e.g., source) a current to the second contact electrode 704. As a current sink, the first source element 712 and the second source element 714 can receive (e.g., sink) current which has traveled through the first contact electrode 702 and the second contact electrode 704, respectively. Current sources and/or sinks can be provided via, for example, one or more current source or sink integrated circuits or other appropriate arrangement of one or more components configured to source or sink current as would be understood by a person having ordinary skill in the art. In various embodiments, the first source element 712 and the second source element 714 can source or sink current, for example, as prescribed by the controller 750, which can provide a signal to the first source element 712 and the second source element 714 to control an amount of current sourced or sunk thereby. Unless specified otherwise, descriptions of embodiments herein in which a source element (e.g., 712, 714) provides a current (e.g., to contact electrodes 702, 704) can similarly describe embodiments in which a source element sinks current. In various examples, a source element (e.g., 712, 714) can provide or emit positive or negative current to a contact electrode (e.g., 702, 704), acting as a current source or a sink. Thus, a source element that provides or emits current is not necessarily limited to a current source, but also can refer to a current sink.

During operation, the controller 750 can be configured to control an amount of current to be sourced from or sunk to a source element, such as source element 712. In some such examples, the controller can provide a digital signal to a digital-to-analog converter (DAC) that controls the amount of current sourced to or sunk from source element, such as described in U.S. patent application Ser. No. 17/109,305, filed Dec. 2, 2020, and entitled COCHLEAR IMPLANT STIMULATION CALIBRATION, which is assigned to the assignee of the instant application and incorporated herein by reference.

In some embodiments, a source element provides a desired current based on a signal received from the controller 750. In some examples, the source element is powered via a compliance voltage provided thereto. The compliance voltage supports the operation of the source element such that the source element is capable of outputting a prescribed current. Thus, the compliance voltage is applied so that the source element "complies" with the controller's prescribed current. In some examples, the controller 750 is configured to control one or more voltage regulators (e.g., via one or more DACs) in order to provide a controllable compliance voltage to one or more source elements. In some cases, a single voltage regulator can provide a corresponding single compliance voltage to each of a plurality of source elements. In other embodiments, a plurality of voltage regulators may be used, for example, to provide individual compliance voltages to individual source elements or to a subset of source elements.

Accordingly, in some embodiments, to operate a given source element (e.g., first source element 712), controller 750 is configured to provide a signal to a corresponding DAC to set the magnitude of current to be sourced/sunk during stimulation. The controller 750 can be further configured to control a voltage regulator to provide a compliance voltage to the source element to provide sufficient operating voltage to support the prescribed current.

In some embodiments, the compliance voltage required to provide a given amount of current from a source element depends on the voltage drop across the stimulated tissue, which is based on the amount of current to be sourced/sunk and the impedance of the tissue through which the current is sourced/sunk. For instance, in some examples, the compliance voltage applied to a source element must be sufficiently large to support the voltage drop across the impedance of the current path as well as any necessary headroom voltage associated with the source element. For example, in some embodiments, each source element comprises one or more transistors (e.g., MOSFETs) and the compliance voltage may be sufficiently large to maintain one transistors of the source element in a saturation mode in order to accurately control the current sourced from/sunk to the source element. For instance, in some examples, the minimum compliance voltage for supporting a prescribed current through a tissue having a given impedance is the sum of the voltage drop across the tissue and a saturation voltage associated with the corresponding source element (e.g., a MOSFET saturation voltage).

Those skilled in the art will recognize that different current source/sink elements may have different levels of required headroom voltage for sustaining a prescribed current across a load. In some embodiments, a controller can be configured to determine a compliance voltage necessary for a given source element to support a given prescribed current in view of the operating characteristics of the source element.

For example, in some embodiments, the current source/sink elements can be feedback driven current sources/sinks. In some such embodiments, the feedback driven current sources/sinks can have a different level of required headroom voltage, and thus a different compliance voltage, for sustaining a prescribed current across a load. For instance, in some examples, a feedback driven current source/sink can include a MOSFET configured to source or sink a prescribed amount of current based on a feedback signal. In some cases, such a current source/sink can operate accurately while the MOSFET is not in saturation mode. Thus, in some embodiments, a compliance voltage for a source element can be independent of a saturation voltage of a MOSFET of the source element.

In some examples, a precision resistor can be used to determine the current being delivered to a patient's cochlear tissue. For instance a controller (e.g., controller 750) can be configured to measure a voltage across the precision resistor and determine the current flowing therethrough. The determined current can be compared to the prescribed current. In some such examples, the current source can be adjusted (e.g., by a controller) such that the current being delivered to a wearers cochlear tissue is the same as the prescribed current. For example, if the delivered current is measured to be less than the prescription current, the current source can be adjusted to increase the supplied current.

In some embodiments, a sufficiently high compliance voltage is required for ensure accurate current sourcing/sinking from source element, for example, to maintain one or more components of the source element in a saturation mode of operation. However, an unnecessarily high compliance voltage may consume excess power and reduce the operating life of the system before a recharge is necessary. For example, operating the source element with a "worst case" compliance voltage high enough to support a prescribed current regardless of the current path impedance may ensure proper operation from the perspective of safely and accurately providing a prescribed current, but may consume more power than necessary to do so. Accordingly, in some embodiments, the controller 750 is configured to adjust the compliance voltage to ensure sufficient voltage to operate the source element accurately while avoiding wasting power due to excess voltage application.

In an example embodiment, if the controller 750 is configured to provide 1 mA of current to the tissue from first source element 712 and first contact electrode 702 and the impedance of the corresponding current path, $Z_{Body1}$, is 1 kΩ, 1V is required to support such current. And if the first source element 712 requires 1V of headroom voltage, a total of 2V is needed to support the 1 mA current across the 1 kΩ impedance and accommodate the 1V headroom. Thus, a compliance voltage of 2V may be applied to the first source element 712 to support providing a 1 mA stimulation via the first contact electrode 702.

In some embodiments, the controller can be configured to determine an appropriate compliance voltage to support desired stimulation from one or more contact electrodes. For example, the controller can be configured to determine the impedance associated with stimulating tissue from each contact electrode and determine, based on the determined impedance, the desired current for stimulation, and the necessary headroom for accurately operating the source element, the appropriate compliance voltage for each such source element.

In some embodiments, the controller 750 can be configured to apply an initial compliance voltage to the first source element 712. The initial compliance voltage can be a sufficiently high voltage to ensure accurate operation of the first source element 712. The controller 750 can be further configured to cause the stimulator 720 to emit a first predetermined electrical current from the first source element 712 to the return electrode 730 via a first current path. In the embodiment of FIG. 7, the first current path starts at the first source element 712, continues to the first contact electrode 702, goes through a wearer's cochlear tissue which has an impedance $Z_{Body1}$, and ends in the return electrode 730. The controller 750 can be configured to determine a first voltage corresponding to a voltage at the first contact electrode 702 relative to a reference voltage 760, for example, by controlling switch 740. In some embodiments, the reference voltage corresponds to a system ground potential. The first voltage corresponding to the voltage at the first electrode 702 may be the voltage at the first electrode or may be another voltage representative thereof, for example, a known percentage of the voltage at the first electrode measured using a voltage divider or the like.

The controller 750 can further be configured to determine a second voltage corresponding to a voltage at the return electrode 730 relative to the reference voltage 760 by controlling switch 740. By determining the first voltage corresponding to the voltage at the first contact electrode 702 and determining the second voltage corresponding to the voltage at the return electrode 730, the controller 750 can determine the voltage drop across the impedance $Z_{Body1}$. As the controller 750 is configured to cause the stimulator 720 to emit a first predetermined current, the controller 750 can determine the first impedance $Z_{Body1}$ associated with the first current path using the first predetermined current and the voltage drop across the first impedance $Z_{Body1}$. In some examples, the controller 750 can be configured to determine the first impedance associated with the first current path based on the determined first voltage, the determined second voltage, and the first predetermined electrical current emitted from the first source element.

In a similar manner, in some embodiments, the controller 750 can be configured to determine a second impedance such as $Z_{Body2}$ of FIG. 7. In some such embodiments, the controller 750 can be configured to apply a second initial compliance voltage to the second source element 714. Further, the controller 750 can be configured to cause the stimulator 720 to emit a second predetermined electrical current from the second source element 714 to the return electrode 730 via a second current path. In some cases, the second predetermined current may be, but need not be, the same as the first predetermined current. In the embodiment of FIG. 7, the second current path starts at the second source element 714, continues to the second contact electrode 704, goes through a wearer's cochlear tissue which has an impedance $Z_{Body2}$, and ends in the return electrode 730. The controller 750 can be configured to determine a third voltage corresponding to a voltage at the second contact electrode 704 relative to a reference voltage 760.

Further, the controller 750 can be configured to determine a fourth voltage corresponding to a voltage at the return electrode 730 relative to the reference voltage 760. By determining the third voltage corresponding to the voltage at the second contact electrode 704 and determining the fourth voltage corresponding to the voltage at the return electrode 730, the controller 750 can determine the voltage drop across the impedance $Z_{Body2}$. As the controller 750 is configured to cause the stimulator 720 to emit a second predetermined current, the controller 750 can determine the second impedance $Z_{Body2}$ associated with the second current path using the second predetermined current and the voltage drop across the second impedance $Z_{Body2}$. Accordingly, in some examples, the controller 750 can be configured to determine the second impedance associated with the second current path based on the determined third voltage, the determined fourth voltage, and the second predetermined electrical current emitted from the second source element.

Once the controller 750 has determined the impedance of a current path, the controller can determine the voltage necessary to source or sink a desired current, which may be the same as or different from the predetermined current value(s) used to determine the impedance values. Based on such voltage and any additional headroom voltage necessary for operating the source element 712, the controller can determine an appropriate compliance voltage for providing the desired current. Such compliance voltage can be provided to the source element (e.g., 712 or 714) in order to operate the source element safely and accurately while avoiding unnecessarily high voltages.

For example, the controller 750 can determine a first compliance voltage for the first source element 712 based on the determined first impedance $Z_{Body1}$ and a first prescribed current for the first source element 712. As discussed elsewhere herein, the first prescribed current can be a current the stimulator 720 uses to simulate a wearer's cochlear tissue during a stimulation operation. Further, in some embodiments, the controller 750 can determine a second compliance voltage for the second source element 714 based on the determined second impedance $Z_{Body2}$ and a prescribed current for the second source element 714. In some embodiments the prescribed current used for determining the second compliance voltage is the same as the first prescribed current. However, in some embodiments, the prescribed current used for determining the second compliance voltage is different from the first prescribed current.

In some embodiments, the controller 750 can also be configured to determine if the determined compliance voltage for providing a prescribed current from a corresponding source element is sufficiently different from an initial compliance voltage, such as that used for determining the impedance associated with a given current path. In some such examples, if the determined compliance voltage is sufficiently different from the initial compliance voltage, the controller 750 can adjust the operation of the corresponding source element such that the compliance voltage is appropriate for the current to be sourced/sunk.

For example, in some embodiments, if the determined first compliance voltage is sufficiently different from the initial compliance voltage, the controller 750 can adjust the compliance voltage of the first source element from the initial compliance voltage to the determined first compliance voltage. In some examples, the first compliance voltage is sufficiently different from the initial compliance voltage if the first compliance voltage is different from the initial compliance voltage at the resolution of the system. In such examples, if any difference between the first compliance voltage and the initial compliance voltage is detected, operation of the first source element is adjusted. In other examples, the first compliance voltage is sufficiently different from the initial compliance voltage if the first compliance voltage is different from the initial compliance voltage at the resolution of the system by a threshold amount, such as a predetermined amount of voltage (e.g., 0.5 V) or percentage (e.g., 10%). In some embodiments, if the determined second compliance voltage is sufficiently different from an initial compliance voltage, the controller 750 can adjust the operation of the second source element (e.g., from using an initial compliance voltage to using a determined second compliance voltage).

While in some embodiments, a controller (e.g., 750) can be configured to adjust a compliance voltage of a source element based on if an initial compliance voltage and a subsequent (e.g., first) compliance voltage are sufficiently different, other control mechanisms are contemplated. For example, in some embodiments, a controller (e.g., 750) can be configured to set a compliance voltage of a source element based on the determined impedance of a wearer's cochlear tissue (e.g., $Z_{Body1}$) and a prescribed current without comparing an initial compliance voltage (e.g., used to determine the impedance) and a determined compliance voltage desired for applying the prescribed current.

Thus, in some embodiments, adjusting the operation of a source element (e.g., 712, 714) comprises adjusting compliance voltage applied to the source element. Adjusting the compliance voltage can include applying a calculated compliance voltage so that the source element is capable of safely providing the prescribed current over the calculated impedance, but does not greatly exceed the necessary voltage and therefore preserves power.

In other examples, adjusting operation of a source element comprises adjusting the prescribed current from a first prescribed current to a second prescribed current and outputting the second prescribed current from the source element. Adjusting the prescribed current from a first prescribed current to a second prescribed current can change the voltage (e.g., compliance voltage) required by the source element to maintain proper operation and minimize power usage. For example, if an initial compliance voltage is insufficient for consistently and accurately providing a prescribed current, the prescribed current can be adjusted to a value that can be predictably provided using the initial compliance voltage.

However, in some embodiments, stimulation of cochlear tissue is based on an amount of charge delivered to the tissue. Since adjusting the prescribed current changes the amount of charge delivered to the cochlear tissue per unit time, if stimulation of a wearer's cochlear tissue is based on an amount of charge, maintaining a predetermined amount of charge delivered to the tissue during stimulation requires adjusting the amount of time the current is delivered. Accordingly, in some embodiments, to maintain the charge delivered to the cochlear tissue, adjusting the current from the first prescribed current to the second prescribed current is accompanied by changing the amount of the time current is provided during stimulation. For example, in some embodiments, if adjusting operation of the source element comprises reducing the amount of prescribed current by 50%, the stimulation signal can be adjusted to apply the current for twice as long as the prescribed current during stimulation. In such operations, the charge delivered to the wearer's cochlear tissue is the same and the amount of current provided is supported by the compliance voltage at the source element.

Adjusting the operation of the source element (e.g., 712, 714) by adjusting the compliance voltage or by adjusting the prescribed current can be advantageous as the controller 750 can maintain safe operation of the cochlear implant system while minimizing power usage.

As discussed elsewhere herein, the compliance voltage of a current source/sink can support the operation of the current source/sink such that it is capable of outputting a prescribed current. In some embodiments, the cochlear implant system is configured to adjust the magnitude of the prescribed current in response to changing magnitudes of detected acoustic stimuli. For example, in some embodiments, when the cochlear implant system is in a relatively quiet environment, the resulting stimulation may be smaller compared to stimulation resulting from louder environments. Thus, in some examples, quieter environments may lead to lower prescribed current magnitudes when compared to louder environments.

In some such embodiments, for quiet environments, the compliance voltage for current sources/sinks can be lowered correspondingly because a reduced prescribed current can be supported by a reduced compliance voltage for a given current path (having a given impedance). Similarly, in some examples, when the cochlear implant system is in a relatively loud environment, the cochlear implant system can be configured to raise the magnitude of prescribed current along with the corresponding compliance voltage to support the higher magnitude of prescribed current.

In some examples, the cochlear implant system can be configured to change the magnitude of prescribed current to adjust to detected acoustic stimuli on an individual electrode basis. In some such examples, the cochlear implant system can be further configured to change the compliance voltage of each current source/sink providing the prescribed current on an individual electrode basis. For example, the cochlear implant system can decrease both the prescribed current and the corresponding compliance voltage of a single current source/sink based on a receiving acoustic stimuli indicative of a quieter environment (e.g., a decrease in loudness).

In some embodiments, the values of the impedances $Z_{Body1}$ and $Z_{Body2}$ of a wearer's cochlear tissue can change over time. Changes to the impedance values can lead to the voltage drop across the impedances associated with a given prescribed current to similarly change over time. In some embodiments, the controller can be configured to determine the impedance of the cochlear tissue (e.g., $Z_{Body1}$ and $Z_{Body2}$ of FIG. 7) for each electrode continuously and adjust the operation of source elements accordingly. In some embodiments, the controller can be configured to determine the impedance of the cochlear tissue (e.g., $Z_{Body1}$ and $Z_{Body2}$ of FIG. 7) for each electrode at intervals and adjust the operation of source elements accordingly. In such embodiments, the controller 750 can repeat the steps for determining the impedance of the cochlear tissue, determining a compliance voltage using the determined impedance and a prescribed current for the source element, and adjusting the operation of the source element if the determined compliance voltage is sufficiently different from an initial compliance voltage.

In some embodiments, the controller 750 is configured to repeat the steps at regular intervals such as at least once per hour. In some embodiments, the controller is configured to repeat the steps once per day or once every minute. The controller 750 can be configured to repeat the steps automatically, however, in some examples, the controller 750 is configured to repeat the steps when prompted (e.g., by a wearer). A person having ordinary skill in the art will appreciate that the controller 750 can be configured to repeat the steps at any interval, regular or irregular, automatic or prompted, and that this disclosure is not limited to the listed embodiments.

In some examples, after the controller 750 has determined the impedance of a wearer's cochlear tissue in a current path (e.g., $Z_{Body1}$), the controller can further compare the impedance to a threshold impedance. If the determined impedance of the cochlear tissue exceeds the threshold impedance, the controller can disable the contact electrode associated with the current path. For example, in the embodiment of FIG. 7, the controller 750 can compare the determined impedance of $Z_{Body1}$ to a threshold impedance, and if the determined impedance of $Z_{Body1}$ exceeds the threshold impedance, the controller can disable the first contact electrode 702. It can be advantageous to disable the contact electrode in such examples as if the determined impedance is too high, the corresponding compliance voltage required may be difficult to produce. Further, if the determined impedance is too high, it could indicate a malfunction of the components in the current path or another issue which is not easily resolved. By disabling the electrode, and thereby the current path, the controller prioritizes safety over possible inaccurate or dangerous operation. In some examples, disabling the contact electrode comprises disabling the corresponding source element, for example, by not applying electrical power thereto.

While controller 750 is shown as a single controller in the embodiment of FIG. 7, in some examples, functionality attributed to the controller 750 is distributed across multiple controllers. For example, in some embodiments, such as shown in FIG. 1, a stimulator and a signal processor may be implemented separately within an implanted system. In some such embodiments, the signal processor is configured to perform one or more functions associated with controller 750, such as providing a stimulation signal to cause one or more source elements to source/sink current.

In some such examples, a stimulator can include a separate controller configured to perform other functions associated with the controller 750 of FIG. 7. For example, such a controller can be configured to perform voltage measurements, such as determining a voltage at a contact electrode and return electrode relative to a reference voltage. In some examples, separate controllers, such as in a stimulator and signal processor, can communicate and act in concert to perform processes described herein.

Figure 8:
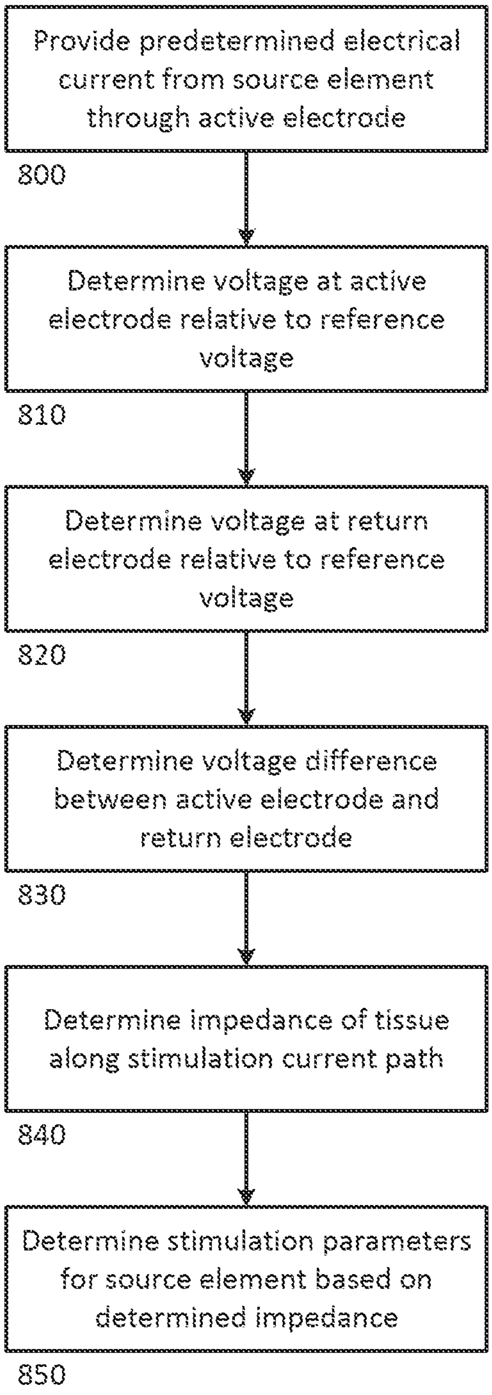
FIG. 8 is an example method for determining and utilizing impedance information for determining one or more stimulation parameters for a cochlear implant system.

FIG. 8 shows an example process for determining and utilizing impedance information for determining one or more stimulation parameters for a cochlear implant system. Such a process can be performed by the system shown in FIG. 7. Such a process can be performed by one or more controllers, such as described elsewhere herein.

In the example of FIG. 8, a source element provides electrical current through an active electrode. In some embodiments, the electrical current is a predetermined current. In step 810, a controller can determine the voltage at the active electrode relative to a reference voltage. In step 820, the controller can further determine the voltage at the return electrode relative to the reference voltage. From the two voltages, the controller can in step 830 determine a voltage difference between the active electrode and the return electrode. This voltage difference can correspond to a voltage drop across an impedance of a current path such as $Z_{Body1}$.

Continuing with step 840, the controller can determine an impedance of the stimulation current path. In some embodiments, the controller uses the voltage difference and the predetermined electrical current to determine the impedance of tissue along the stimulation current path, for example, using Ohm's law.

Once the impedance of the tissue along the stimulation path is determined, the system can determine one or more stimulation parameters for the source element based on the determined impedance as in step 850. For example, if a prescribed current is to be used for stimulation, the system (e.g., via one or more controllers) can determine an appropriate compliance voltage to provide to the source element for supporting the prescribed current. In other examples, determining one or more stimulation parameters comprises determining a current that can be sourced/sunk by the source element across the impedance for a given compliance voltage. As described elsewhere herein, in some examples, the system can deliver a specified amount of charge during stimulation. Systems can be configured to determine a current based on the determined impedance and a compliance voltage, and then determine an amount of time to apply such current in order to achieve a desired amount of delivered charge.

Figure 9:
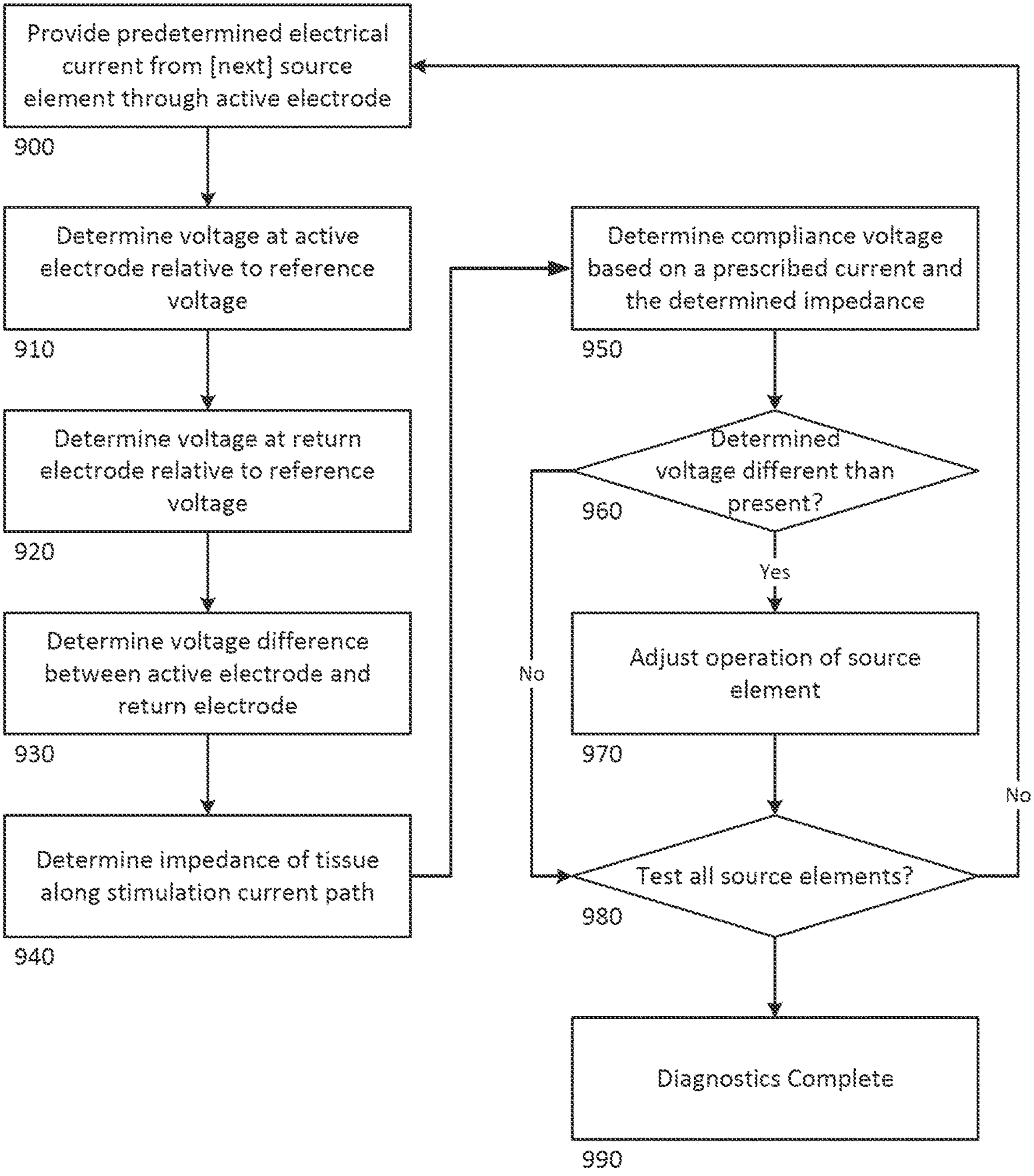
FIG. 9 is an example method of adjusting operation of a cochlear implant system.

In some cases, the system can be configured to update operation of a source element based on determined impedance values. FIG. 9 is an example method of adjusting operation of a cochlear implant system. In the illustrated method, a controller is configured to perform the steps, however, in some embodiments, a stimulator, signal processor or other device/devices can perform the steps of FIG. 9. Starting with step 900, a source element provides electrical current through an active electrode. In some embodiments, the electrical current is a predetermined current. In step 910, a controller can determine the voltage at the active electrode relative to a reference voltage. In step 920, the controller can further determine the voltage at the return electrode relative to the reference voltage. From the two voltages, the controller can in step 930 determine a voltage difference between the active electrode and the return electrode. This voltage difference can correspond to a voltage drop across an impedance of a current path such as $Z_{Body1}$.

Continuing with step 940, the controller can determine an impedance of the stimulation current path. In some embodiments, the controller uses the voltage difference and the predetermined electrical current to determine the impedance of tissue along the stimulation current path, for example, using Ohm's law. In step 950, the controller can determine a compliance voltage for the source element based on a prescribed current and the determined impedance. In some embodiments, the prescribed current is the predetermined current, and in other embodiments, the prescribed current is different from the predetermined current.

In step 960, the controller determines if the compliance voltage is different than the present compliance voltage. In some embodiments, the present compliance voltage is an initial compliance voltage applied to the source element to provide the predetermined electrical current in step 900. In some embodiments, the controller can determine if the compliance voltage is sufficiently different than the present voltage. As described elsewhere herein, in some cases, any difference between the determined compliance voltage and the present voltage is considered sufficient for adjustment, while in other cases, threshold differences may be used. In the case that the determined compliance voltage is sufficiently different from the present voltage, the method can continue with step 970, in which the controller adjusts operation of the source element, such as described elsewhere herein. For instance, in some embodiments, the adjustment includes applying the determined compliance voltage to the source element, and in some embodiments, the adjustment includes changing the output current (e.g., prescribed current) of the source element and the amount of time the current is output.

In the case that the determined compliance voltage is not different or is not sufficiently different from the present voltage, the method continues with step 980, in which the controller determines if all the source elements have been tested. If all the source elements have been tested, the diagnosis is complete, and the method ends at step 990. However, if not all the source elements have been tested, the method begins again at step 900 for a different source element and active electrode.

In general, the process of FIG. 9 can be performed for each of a plurality of source elements, each corresponding to one of a plurality of contact electrodes. In some examples, a unique compliance voltage can be applied to each source element as determined using a process such as that shown in FIG. 9. In other examples, the same compliance voltage can be applied to a plurality of, or all of, the source elements. In some such examples, the compliance voltage applied at each source element is the maximum compliance voltage of the compliance voltages determined for each of the source elements. Thus, each source element will be able to safely and accurately source or sink a prescribed current at the provided compliance voltage. As described elsewhere herein, in some embodiments, source elements having an impedance value higher than a threshold impedance (or similarly requiring a compliance voltage higher than a threshold voltage) can be disabled so that such outlier values do not lead to excessively high compliance voltages at each source element. In some cases, such outlier impedance values can be cause by damaged or broken contact electrodes and/or a poor interface between the contact electrode and surrounding fluid or tissue.

While the steps of FIG. 9 have been described as being done in a specific order, a person having ordinary skill in the art will recognize the steps need not be performed in order. In some embodiments, different steps can be done at different times and, in some embodiments, some steps can be performed at the same time as other steps.

As described elsewhere herein, in some embodiments, the controller can be configured to continuously determine the impedance of the current path through the wearer's cochlear tissue (e.g., $Z_{Body1}$ and $Z_{Body2}$) for each electrode and adjust the operation of source elements accordingly. For example, the controller can be configured to measure the voltage drop across the current path while providing electrical stimuli of a prescribed current through the current path and determine the impedance associated therewith in real time. Thus, in some examples, the processes shown in FIGS. 8 and/or 9 can be performed in real time.

In some embodiments, the controller (e.g., 750) is configured to perform or repeat the process of in FIG. 8 and/or FIG. 9 at regular intervals such as at least once per hour. In some embodiments, the controller is configured to repeat the steps once per day or once every minute. The controller can be configured to repeat the steps automatically, however, in some examples, the controller is configured to repeat the steps when prompted (e.g., by a wearer or audiologist). A person having ordinary skill in the art will appreciate that the controller 750 can be configured to repeat the steps at any interval, regular or irregular, automatic or prompted, and that this disclosure is not limited to the listed embodiments. Such processes can be performed during an initial system fitting and/or can be performed as part of a maintenance process or in order to address system operation problems (e.g., if a changing impedance impacts operation of the system or an electrode becomes inoperable).

In some examples, a process similar to that of FIGS. 8 and/or 9 can be used for feedforward compliance voltage control. For example, in some embodiments, prior to stimulating the tissue with a prescribed current the controller can be configured to determine and apply an appropriate compliance voltage for providing the prescribed current via methods described herein. Thus, as described herein, in some embodiments, the system can be configured to update compliance voltage values according to the determined impedance in real time in order to provide enough voltage to support a prescribed current and increase the compliance voltage only as necessary to accommodate changes in the impedance and/or prescribed current. Such compliance voltage control can save power compared to systems that constantly apply a "worst case" compliance voltage to always accommodate a wide range of impedance and current values.

In some embodiments, the compliance voltage applied to a source element can be one from a predetermined list of possible compliance voltage settings. For instance, in some embodiments, there can be a discrete number of voltage bins, each associated with a predefined compliance voltage (e.g., the upper bound of the voltage bin). In some such embodiments, a controller can be configured to determine an appropriate compliance voltage for a given source element based on a measured impedance and a prescribed current as described herein. The controller can determine in which voltage bin the determined compliance voltage falls and apply the corresponding predetermined compliance voltage to that source element.

For instance, in an example embodiment, a controller programmed with three voltage bins (e.g., 2-4V, 4-8V, and 8-16V) can determine, for a given source element, a compliance voltage based on a measured impedance and prescribed current value and in which voltage bin the compliance voltage falls. The controller can be configured to provide a predetermined compliance voltage to the source element corresponding to the determined bin, such as the upper bound of the determined bin. In various embodiments, any number and size of voltage bins and corresponding predetermined compliance voltages can be used can be used. For instance, in another example, a controller can be programmed with voltage bins of 2-4V, 4-8V, 8-12V, and 12-16V.

In some embodiments, a controller can be configured to determine an appropriate compliance voltage for each of a plurality of source elements. In other examples, a controller can be configured to determine a compliance voltage appropriate for application to a plurality of source elements. For example, in some such embodiments, the controller is configured to determine a compliance voltage for each of a plurality of source elements based on corresponding determined impedances and prescribed current values and apply, to each of the plurality of source elements, the highest of the determined compliance voltages. In some such examples, a single voltage regulator or other components can be used to apply the compliance voltage to a plurality of source elements, and each of the plurality of source elements will be provided with enough voltage to provide its corresponding prescribed current.

In some examples, a single compliance voltage is provided to all source elements. In other examples, source elements can be grouped together into subsets of source elements and the same compliance voltage can be provided to each source element for a given subset. In general, any number of source elements can be used to provide electrical stimulation via corresponding contact electrodes. For instance, in some examples, the cochlear implant system includes 16 contact electrodes and corresponding source elements, divided into four groups (e.g., four groups of four source elements). For a stimulation, each contact electrode will have a prescribed current to be emitted via its corresponding source element and impedance of the current path associated with each contact electrode. Accordingly, the controller can be configured to determine an appropriate compliance voltage for each corresponding source element.

The controller can be further configured for, for a given group of source elements, provide a single compliance voltage to each source element, such as the determined compliance voltage that is the highest among the source elements in the group. Thus, the controller can determine a compliance voltage for each source element and a compliance voltage for each group of source elements based on the determined compliance voltages of the source elements in the group. In some embodiments, such a process can be performed using compliance voltage bins such as described herein. For instance, in some such examples, the controller can be configured to determine which of a predetermined plurality of compliance voltages to apply for a given group of source elements.

In general, a cochlear electrode can include any number of contact electrodes for providing electrical stimulation to surrounding tissue and fluid. A stimulator can include a corresponding plurality of source elements, each configured to source or sink current to or from the tissue or fluid via the corresponding contact electrode. In some examples, the controller can determine and provide a corresponding compliance voltage to each source element. In other examples, source elements can be arranged into groups wherein each source element within the group receives the same compliance voltage. The source elements can be divided into any number of groups, and the groups can include any number of source elements. Groups need not be the same size.

In some examples, the controller can be configured to define groups of source elements, for example, based on determined compliance voltages for each source element. For instance, in an example embodiment, the controller can be configured to determine a compliance voltage for each source element and group together source elements having a similar determined compliance voltage or whose compliance voltages fall within the same predefined voltage bin.

In some such examples, the controller is configured to group source elements and corresponding electrodes according to compliance voltage and determine a stimulation sequence based on the determined groups. For instance, in some embodiments, the controller can be configured to provide electrical stimulation via a plurality of source elements sequentially.

In an example implementation, the controller can group the source elements into three groups, each group having a corresponding compliance voltage, such as described elsewhere herein. The controller can be configured to apply a first compliance voltage to the plurality of source elements in a corresponding first group of source elements and sequentially provide electrical stimulation via each of the source elements in the first group. The controller can adjust the compliance voltage to a second compliance voltage and apply the second compliance voltage to a corresponding second group of source elements and sequentially provide electrical stimulation via each of the source elements in the second group. Finally, the controller can adjust the compliance voltage to the third compliance voltage and apply the third compliance voltage to a corresponding third group of source elements and sequentially provide electrical stimulation via each of the source elements in the second group. The controller can then adjust eh compliance voltage to the first compliance voltage and repeat the process.

In some such examples, the controller can be configured to cycle through each of a plurality of source elements while providing an appropriate compliance voltage to support the desired operation of each source element. Grouping the source elements by compliance voltage allows the controller to do so with minimal adjustments to the compliance voltage.

In some examples, the controller is configured to group source elements based on compliance voltage and provide electrical stimulation via multiple source elements within the group simultaneously. For example, in an example having three groups and three corresponding compliance voltages (first, second, and third compliance voltages), the controller can be configured to provide the first compliance voltage to the source elements in the first group and provide electrical stimulation simultaneously via each source element within the first group. The controller can then adjust the compliance voltage to the second compliance voltage and provide electrical stimulation simultaneously via each source element within the second group. Similarly, the controller can then adjust the compliance voltage to the third compliance voltage and provide electrical stimulation simultaneously via each source element within the third group. The controller can repeat the process by adjusting the compliance voltage back to the first compliance voltage and providing stimulation via the source elements in the first group.

In some examples, providing a compliance voltage to source elements within a group of source elements (e.g., providing a first compliance voltage to source elements within a first group of source elements), includes providing the first compliance voltage to all source elements. For instance, the controller can be configured to adjust a system-wide compliance voltage that is applied to all source elements, even if the controller applies electrical stimulation via a subset thereof (e.g., via source elements within a first group) before adjusting a compliance voltage. In other examples, the controller can be configured to provide the first compliance voltage to those source elements within the first group of source elements and not to source elements not within the first group.

Various non-limiting embodiments have been described. These and others are within the scope of the following claims.

The invention claimed is:

1. A cochlear implant system comprising:

a cochlear electrode comprising a plurality of contact electrodes, the plurality of contact electrodes including a first contact electrode;

a stimulator in electrical communication with the cochlear electrode, the stimulator comprising a first source element in electrical communication with the first contact electrode;

a return electrode; and one or more controllers configured to:

for each of the plurality of contact electrodes:

determine an impedance associated with a current path associated with electrical stimulation between the contact electrode and the return electrode; and determine a compliance voltage associated with electrical stimulation via the contact electrode based on the determined impedance and a prescribed current;

apply the determined compliance voltage associated with electrical stimulation via the first contact electrode to the first source element;

determine a subsequent compliance voltage associated with applying a first subsequent prescribed current via the first contact electrode using the first source element; and if the determined subsequent compliance voltage associated with applying the first subsequent prescribed current via the first contact electrode using the first source element is sufficiently different from the applied determined compliance voltage associated with electrical stimulation via the first contact electrode, adjust the prescribed current from the first subsequent prescribed current to a second subsequent prescribed current and cause the first source element to output the second subsequent prescribed current via the first contact electrode.

2. The cochlear implant system of claim 1, wherein the first source element comprises a current sink.

3. The cochlear implant system of claim 1, wherein the one or more controllers are configured to control a voltage regulator to apply the determined compliance voltage to the first source element.

4. The cochlear implant system of claim 1, wherein the stimulator further comprises a second source element configured to provide electrical current to a second contact electrode of the plurality of contact electrodes.

5. The cochlear implant system of claim 1, wherein the first source element comprises a metal oxide semiconductor field effect transistor (MOSFET) having a saturation region and a triode region of operation, and wherein the compliance voltage associated with electrical stimulation via the first contact electrode comprises a sufficient voltage to maintain the MOSFET in the saturation region.

6. The cochlear implant system of claim 1, wherein determining the compliance voltage associated with electrical stimulation via the first contact electrode comprises:

applying an initial compliance voltage to the first source element;

causing the stimulator to emit a first predetermined electrical current from the first source element to the return electrode via a first current path;

determining a first voltage corresponding to a voltage at the first contact electrode relative to a reference voltage;

determining a second voltage corresponding to a voltage at the return electrode relative to the reference voltage;

determining a voltage difference between the first voltage and the second voltage;

determining an impedance of the first current path based on the determined voltage difference and the first predetermined electrical current; and determining the compliance voltage associated with electrical stimulation via the first contact electrode based on the determined impedance and the prescribed current.

7. The cochlear implant system of claim 6, further comprising a signal processor in communication with the stimulator; and wherein:

the one or more controllers comprise a first controller and a second controller;

the signal processor comprises the first controller, and the first controller is configured to cause the stimulator to emit the first predetermined electrical current from the first source element; and the stimulator comprises the second controller, and the second controller is configured to determine the first voltage and the second voltage.

8. The cochlear implant system of claim 1, wherein the one or more controllers are further configured to, if, for one of the plurality of contact electrodes, the determined impedance associated with the current path associated with electrical stimulation between the contact electrode and the return electrode exceeds a predetermined threshold, disable the contact electrode.

9. The cochlear implant system of claim 1, wherein applying the determined compliance voltage to the first source element comprises applying the voltage associated with electrical stimulation via the first contact electrode to the first source element.

10. The cochlear implant system of claim 1, wherein the one or more controllers are configured to determine a single compliance voltage associated with electrical stimulation at each of the plurality of contact electrodes.

11. The cochlear implant system of claim 1, wherein determining the compliance voltage associated with electrical stimulation via a given contact electrode comprises determining a voltage from a predetermined list of possible compliance voltages.

12. The cochlear implant system of claim 1, wherein the stimulator comprises a plurality of source elements, each of the plurality of source elements being in electrical communication with a corresponding one of the plurality of contact electrodes.

13. The cochlear implant system of claim 1, wherein the one or more controllers are configured to, after applying the determined compliance voltage to the first source element:

determine an updated impedance associated with the current path associated with electrical stimulation between the first contact electrode and the return electrode; and wherein determining the subsequent compliance voltage associated with applying the first subsequent prescribed current via the first contact electrode using the first source element is based on the determined updated impedance.

14. The cochlear implant system of claim 13, wherein the one or more controllers are configured to:

determine a first amount of time for applying the first subsequent prescribed current via the first contact electrode; and determine an updated amount of time for applying the second subsequent prescribed current via the first contact electrode, the updated amount of time being such that a total charge that would be delivered by applying the first subsequent prescribed current for the first amount of time is approximately equal to a total charge that would be delivered by applying the second subsequent prescribed current for the updated amount of time.

15. The cochlear implant system of claim 1, wherein the one or more controllers are configured to, after determining the compliance voltage for each of the plurality of contact electrodes, determine a maximum compliance voltage and apply the determined maximum compliance voltage to the first source element.

16. The cochlear implant system of claim 1, wherein the one or more controllers are configured to:

determine a first amount of time for applying the first subsequent prescribed current via the first contact electrode; and determine an updated amount of time for applying the second subsequent prescribed current via the first contact electrode, the updated amount of time being such that a total charge that would be delivered by applying the first subsequent prescribed current for the first amount of time is approximately equal to a total charge that would be delivered by applying the second subsequent prescribed current for the updated amount of time.

17. A cochlear implant system comprising:

a cochlear electrode comprising a plurality of contact electrodes, the plurality of contact electrodes including a first contact electrode;

a stimulator in electrical communication with the cochlear electrode, the stimulator comprising a first source element in electrical communication with the first contact electrode;

a return electrode; and one or more controllers configured to:

determine an impedance associated with a current path associated with electrical stimulation between the first contact electrode and the return electrode;

determine a first compliance voltage associated with electrical stimulation via the first contact electrode based on the determined impedance and a prescribed current; and apply the determined first compliance voltage to the first source element;

determine a subsequent compliance voltage associated with applying a first subsequent prescribed current via the first contact electrode using the first source element; and if the determined subsequent compliance voltage is sufficiently different from the first compliance voltage, adjust the prescribed current from the first subsequent prescribed current to a second subsequent prescribed current and cause the first source element to output the second subsequent prescribed current via the first contact electrode.

18. A method of adjusting operation of a cochlear implant system comprising:

determining an impedance associated with a current path associated with electrical stimulation of cochlear tissue between a contact electrode and a return electrode;

determining a compliance voltage associated with electrical stimulation of cochlear tissue via the contact electrode based on the determined impedance and a prescribed current;

applying the determined compliance voltage associated with electrical stimulation of cochlear tissue via the contact electrode to a source element;

determining a subsequent compliance voltage associated with applying a first subsequent prescribed current via the contact electrode using the source element;

determining that the determined subsequent compliance voltage is sufficiently different from the applied determined compliance voltage; and in response to the determined subsequent compliance voltage being sufficiently different from the applied determined compliance voltage, adjusting the prescribed current from the first subsequent prescribed current to a second subsequent prescribed current and causing the source element to output the second subsequent prescribed current via the contact electrode.

19. The method of claim 18, further comprising determining an updated impedance associated with the current path associated with electrical stimulation of cochlear tissue between the contact electrode and the return electrode; and wherein determining the subsequent compliance voltage associated with applying the first subsequent prescribed current via the contact electrode using the source element is based on the determined updated impedance.

20. The method of claim 19, further comprising:

determining a first amount of time for applying the first subsequent prescribed current via the contact electrode; and determining an updated amount of time for applying the second subsequent prescribed current via the contact electrode, the updated amount of time being such that a total charge that would be delivered by applying the first subsequent prescribed current for the first amount of time is approximately equal to a total charge that would be delivered by applying the second subsequent prescribed current for the updated amount of time.

21. The method of claim 18, wherein the steps of the method are performed by one or more controllers of an implantable system.

22. The method of claim 21, wherein the steps of the method are performed in response to a received prompt.

23. The method of claim 21, wherein the steps of the method are repeated automatically according to a schedule.

* * * * *